United States Patent
Mistretta et al.

[19]

[11] Patent Number: 5,873,825
[45] Date of Patent: Feb. 23, 1999

[54] THREE DIMENSIONAL DIGITAL SUBTRACTION MAGNETIC RESONANCE ANGIOGRAPHY WITH LIMITED K-SPACE MASK

[75] Inventors: Charles A Mistretta; Frank R Korosec; Thomas M Grist; Richard Frayne, all of Madison, Wis.

[73] Assignee: Wisconsin Alumni Research Foundation, Madison, Wis.

[21] Appl. No.: 55,501

[22] Filed: Apr. 6, 1998

Related U.S. Application Data

[60] Provisional application No. 60/043,531 Apr. 11, 1997.
[51] Int. Cl.$^6$ .................................................... A61B 5/055
[52] U.S. Cl. ........................ 600/401; 600/419; 600/420; 324/307; 324/309
[58] Field of Search ................................... 600/410, 419, 600/420; 324/306, 307, 309, 312

[56]  References Cited

U.S. PATENT DOCUMENTS

| | | | |
|---|---|---|---|
| 4,204,225 | 5/1980 | Mistretta | 358/111 |
| 4,204,226 | 5/1980 | Mistretta | 358/111 |
| 4,417,213 | 11/1983 | Prince | 128/653.3 |
| 4,830,012 | 5/1989 | Riederer | 128/653 |
| 4,918,396 | 4/1990 | Dumoulin et al. . | |
| 4,986,272 | 1/1991 | Riederer et al. . | |
| 5,166,875 | 11/1992 | Machida . | |
| 5,204,627 | 4/1993 | Mistretta et al. . | |
| 5,303,706 | 4/1994 | Moshfeghi . | |
| 5,348,011 | 9/1994 | NessAiver . | |
| 5,377,680 | 1/1995 | Berstein et al. | 128/653.2 |
| 5,417,213 | 5/1995 | Prince | 128/655.3 |
| 5,435,303 | 7/1995 | Berstein et al. . | |
| 5,474,067 | 12/1995 | Laub | 128/653.2 |
| 5,485,086 | 1/1996 | Meyer et al. | 324/307 |
| 5,498,961 | 3/1996 | Kuhn et al. | 324/309 |
| 5,553,619 | 9/1996 | Prince . | |
| 5,653,233 | 8/1997 | Pelc et al. | 128/653.2 |
| 5,713,358 | 2/1998 | Mistretta et al. | 128/653.2 |

FOREIGN PATENT DOCUMENTS

| | | |
|---|---|---|
| 0 599 456 A1 | 1/1994 | European Pat. Off. . |
| 405329126 | 12/1993 | Japan . |
| 406000170 | 1/1994 | Japan . |
| 406169896 | 6/1994 | Japan . |

OTHER PUBLICATIONS

*Block Regional Interpolation Scheme for k–space(BRISK): A Rapid Cardiac Imaging Technique;* MRM 33:163–170; Doyle, et al.

*Improved Ejection Fraction and Flow Velocity Estimates with Use of View Sharing and Uniform Repetition Time Excitation with Fasr Cardiac Techniques;* Radiology 1995; 195:417–478; Foo, et al.

*Block Regional Interpolation Scheme for k–space (Brisk): A Rapid Cardiac Imaging Technique;* MRM 33:163–170 (1995); Doyle et al.

*Breath–hold Cine MR Imaging with a Shared and Reordered Gradient Echo Technique;* Siemens Medical Engineering; Erlangen, Germany, p. 478.

*Primary Examiner*—Marvin M. Lateef
*Assistant Examiner*—Eleni Mantis Mereader
*Attorney, Agent, or Firm*—Quarles & Brady, LLP

[57] ABSTRACT

A dynamic MRA study of a subject is performed using a 3D fast gradient-recalled echo pulse sequence. The frame rate of the resulting series of reconstructed images is increased by sampling a central region of k-space at a higher rate than the peripheral regions of k-space. A difference image is produced by subtracting a mask formed by central region k-space sampling from a selected image frame formed by central region and peripheral regions k-space sampling.

4 Claims, 6 Drawing Sheets

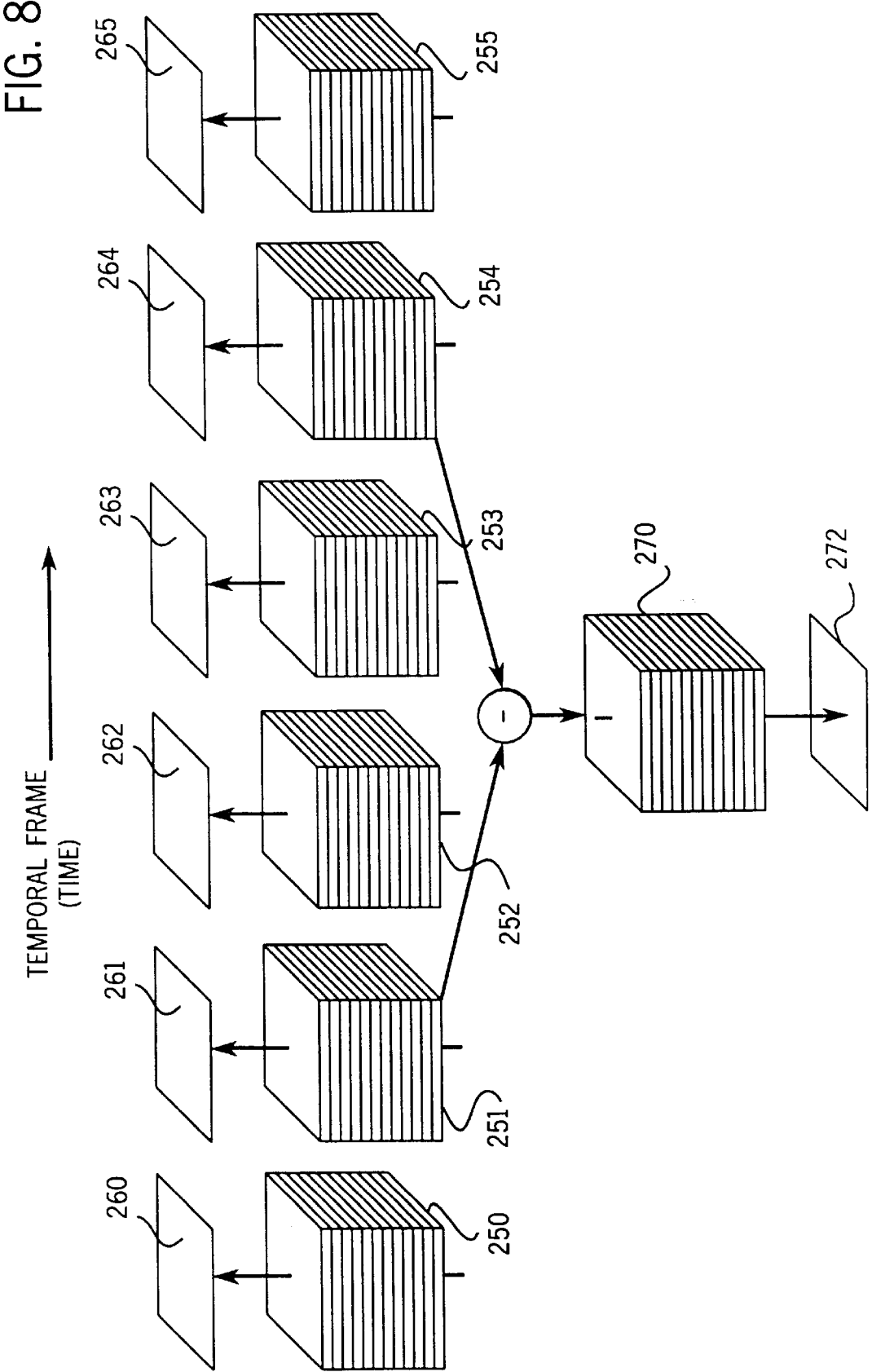

THREE DIMENSIONAL DIGITAL SUBTRACTION MAGNETIC RESONANCE ANGIOGRAPHY WITH LIMITED K-SPACE MASK

This invention was made with United States Government support awarded by NIH Grant Nos.: R01-HL51370; R29-HL57501; and K08-HL02848. The United States Government has certain rights in this invention.

BACKGROUND OF THE INVENTION

This is a provisional application Ser. No. 60/043,531 filed Apr. 11, 1997.

The field of the invention is magnetic resonance angiography ("MRA"), and particularly, dynamic studies of the human vasculature using contrast agents which enhance the NMR signals.

Diagnostic studies of the human vasculature have many medical applications. X-ray imaging methods such as digital subtraction angiography ("DSA") have found wide use in the visualization of the cardiovascular system, including the heart and associated blood vessels. Images showing the circulation of blood in the arteries and veins of the kidneys and the carotid arteries and veins of the neck and head have immense diagnostic utility. Unfortunately, however, these x-ray methods subject the patient to potentially harmful ionizing radiation and often require the use of an invasive catheter to inject a contrast agent into the vasculature to be imaged.

One of the advantages of these x-ray techniques is that image data can be acquired at a high rate (i.e. high temporal resolution) so that a sequence of images may be acquired during injection of the contrast agent. Such "dynamic studies" enable one to select the image in which the bolus of contrast agent is flowing through the vasculature of interest. Earlier images in the sequence may not have sufficient contrast in the suspect vasculature, and later images may become difficult to interpret as the contrast agent reaches veins and diffuses into surrounding tissues. Subtractive methods such as that disclosed in U.S. Pat. No. 4,204,225 entitled "Real-Time Digital X-ray Subtraction Imaging" may be used to significantly enhance the diagnostic usefulness of such images.

Magnetic resonance angiography (MRA) uses the nuclear magnetic resonance (NMR) phenomenon to produce images of the human vasculature. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the spins, and after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals, are digitized and processed to reconstruct the image using one of many well known reconstruction techniques.

Most NMR scans currently used to produce medical images require many minutes to acquire the necessary data. The reduction of this scan time to seconds rather than minutes is the major obstacle in performing clinical dynamic studies using MRI methods. The most common MRI method currently used for non-triggered, time-resolved imaging is to use an echoplanar imaging ("EPI") pulse sequence such as that first described by Peter Mansfield (J. Phys. C. 10: L55–L58, 1977). In principle the EPI scan enables imaging of dynamic process occurring with periods measured on the order of a few hundred milliseconds. However, time-resolved EPI is otherwise unsuitable for contrast enhanced MRA because it exhibits a low contrast between blood and surrounding tissues due to the long time intervals (e.g. 100 ms) between RF excitations. EPI also has enhanced sensitivity to a variety of flow-related artifacts, and EPI images can be blurred due to $T_2^*$-modulation of k-space.

A number of methods have been developed to increase the temporal resolution of MRI scans using pulse sequences that are applicable to MRA. In a method known in the art as "MR fluoroscopy" and described in U.S. Pat. No. 4,830,012, the subject is scanned by continuously and repeatedly acquiring the N phase encoding views needed for a complete image. Rather than waiting for an entirely new set of N views before reconstructing the next image, however, images are reconstructed at a much higher rate by using the most recent N views. In other words, an image is reconstructed from newly acquired views as well as views used in reconstructing previous images in the dynamic study. While very high temporal rates are achieved with MR fluoroscopy, the image contrast is not satisfactory for MRA because the central views in k-space, which dominate the overall image contrast, are still updated at the much slower inherent scan rate (i.e. NxTR).

Another method for increasing temporal resolution of MRI images is referred to in the art as "keyhole" imaging. As described, for example, by R. A. Jones, et al. in "Dynamic, Contrast Enhanced, NMR Perfusion Imaging Of Regional Cerebral Ischaemia In Rats Using K-Space Substitution", *SMR Eleventh Annual Meeting* 1992 abs. 1138, a sequence of images is acquired during a dynamic study in which a contrast agent is injected in the subject. The first image in the sequence is a reference image in which all the phase encoding views (e.g. 128 views) are acquired. Subsequent images are produced, however, by only acquiring the central views (e.g. the central 32 views). These keyhole scans can obviously be acquired much faster than complete scans and the temporal rate is increased proportionately. The keyhole images are reconstructed using the most recent central k-space views combined with the outer, peripheral k-space views from the reference scan. Unfortunately, in situations where the low spatial frequency changes in the reconstructed images do not capture the evolution of the dynamic study, k-space keyhole imaging is not appropriate. This is a problem when contrast changes in small regions are to be studied, and in such studies the number of central views acquired must be increased to the point where the gain in temporal resolution is lost.

Related to the k-space keyhole imaging method is a method known in the art as limited field of view ("FOV") dynamic imaging. As described, for example, by Hu and Parrish, published in *Magnetic Resonance in Medicine*, Vol. 31, pp. 691–694, 1994, and by Frederickson and Pelc, 3rd SMR, 1, 197.1995; this method is applied to dynamic studies in which the changing part of the image occupies no more than one half the full FOV. A reference image representing the static part of the image is produced at the beginning of the study and a series of images encompassing only the dynamic, central portion of the image are produced using half the number of phase encoding views. These dynamic images can be acquired at a higher temporal rate because only half the number of views (either the odd or even views) need be acquired. The dynamic and static portions of the image are combined to produce a corresponding series of full FOV images. of course, if changes occur in the static portion of the image, the information obtained from these regions will no longer accurately remove artifacts aliased into the small FOV.

MR angiography (MRA) has been an active area of research. Two basic techniques have been proposed and evaluated. The first class, time-of-flight (TOF) techniques, consists of methods which use the motion of the blood relative to the surrounding tissue. The most common approach is to exploit the differences in signal saturation that exist between flowing blood and stationary tissue. This is known as flow-related enhancement, but this effect is misnamed because the improvement in blood-tissue contrast is actually due to the stationary tissues experiencing many excitation pulses and becoming saturated. Flowing blood, which is moving through the excited section, is continually refreshed by spins experiencing fewer excitation pulses and is, therefore, less saturated. The result is the desired image contrast between the high-signal blood and the low-signal stationary tissues.

MR methods have also been developed that encode motion into the phase of the acquired signal as disclosed in U.S. Pat. No. Re. 32,701. These form the second class of MRA techniques and are known as phase contrast (PC) methods. Currently, most PC MRA techniques acquire two images, with each image having a different sensitivity to the same velocity component. Angiographic images are then obtained by forming either the phase or complex difference between the pair of velocity-encoded images. Phase contrast MRA techniques have been extended so that they are sensitive to velocity components in all three orthogonal directions.

Despite the tremendous strides made in recent years, at many clinical sites MRA is still considered a research tool and is not routinely used in clinical practice. More widespread application of either TOF or PC techniques is hampered by the presence of a variety of deleterious image artifacts, which can mask and, in some cases, even mimic pathology. These artifacts generally result in a lower specificity, as well as compromised sensitivity.

To enhance the diagnostic capability of MRA a contrast agent such as gadolinium can be injected into the patient prior to the MRA scan. As described in U.S. Pat. No. 5,713,358, a series of images are acquired which depict the subject as the contrast agent enters the region being imaged.

A reference image, or "mask," which depicts the subject before contrast agent arrives at the region of interest is subtracted from one of these images to remove the static tissues and further highlight the vasculature into which the contrast agent flows.

SUMMARY OF THE INVENTION

The present invention is an improved method for performing contrast enhanced MR angiography. More specifically, an NMR pulse sequence is performed over a period of time to sample a region of k-space, a NMR mask data set is formed from samples of k-space from a central region therein, an NMR image data set is formed from other samples of k-space, including samples from the central region and samples from peripheral regions therein, the NMR mask data set is subtracted from the NMR image data set, and an image is produced from the difference data set.

A general object of the invention is to produce a subtraction MR angiogram in which the high spatial frequency information is maintained. By limiting the spatial frequency of the NMR mask data set to the central region of k-space, high spatial frequency information is retained in the difference data set. As a result, detailed features are present in the reconstructed image.

BRIEF DESCRIPTION OF THE DRAWINGS

FIG. 8 is a pictorial representation of the data sets for each image frame in the dynamic study and how they are combined to produce an MRA image.

DESCRIPTION OF THE PREFERRED EMBODIMENT

Figure 1:
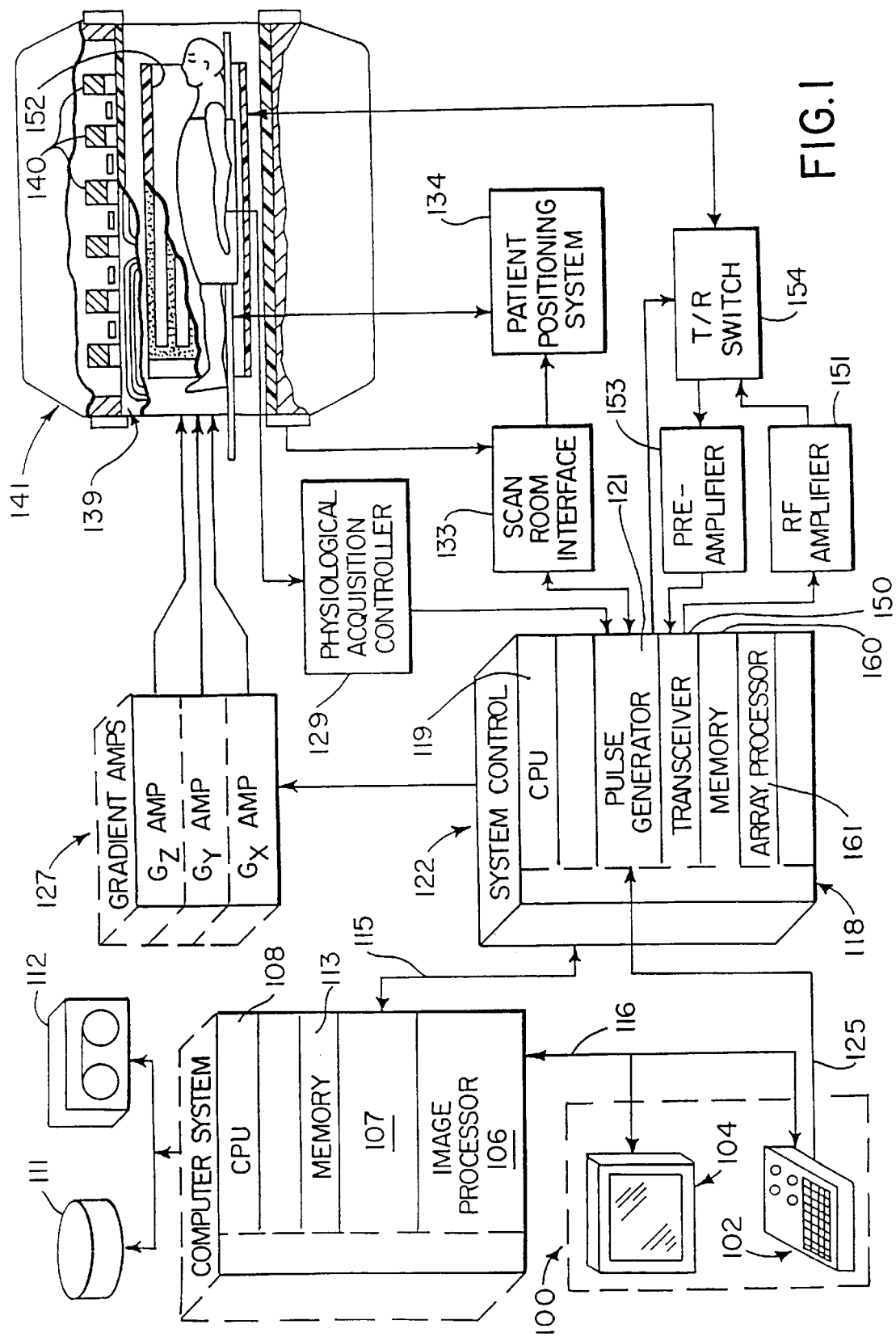
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. it produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RP coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

Figure 2:
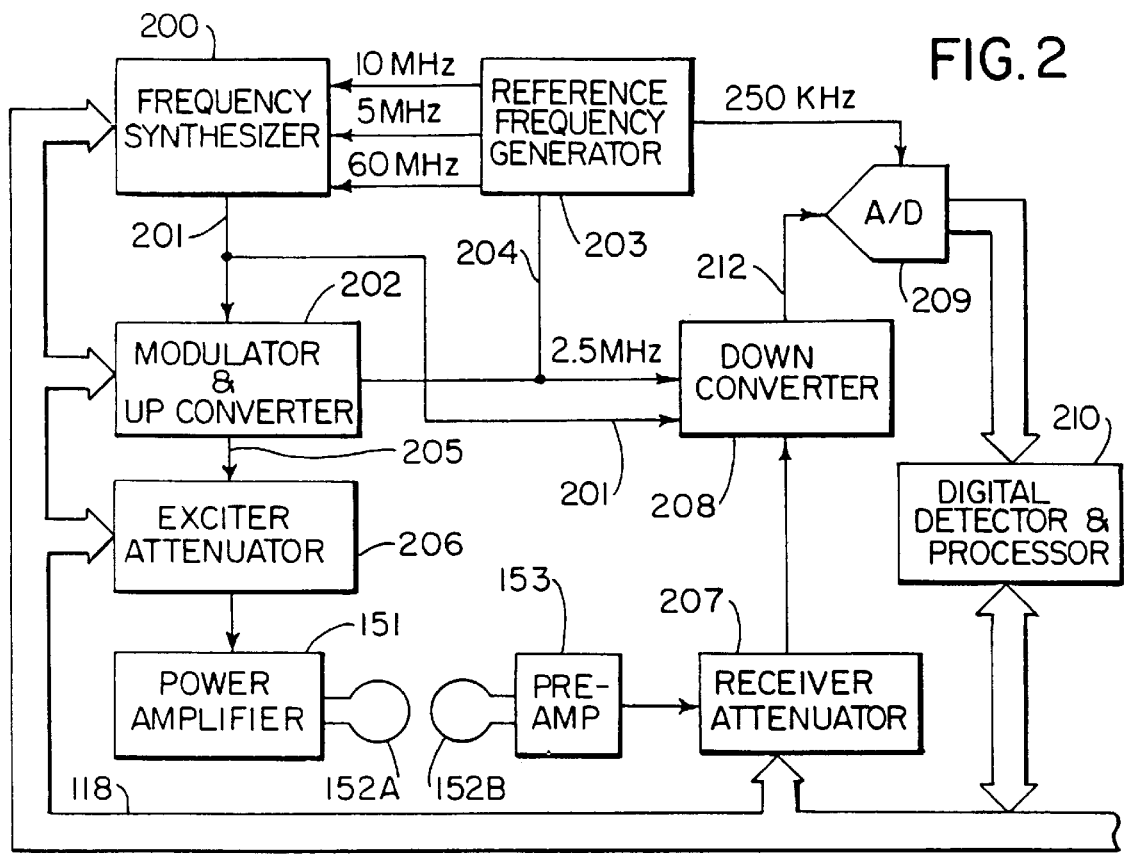
FIG. 2 is an electrical block diagram of the transceiver which forms part of the MRI system of FIG. 1.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

Figure 3:
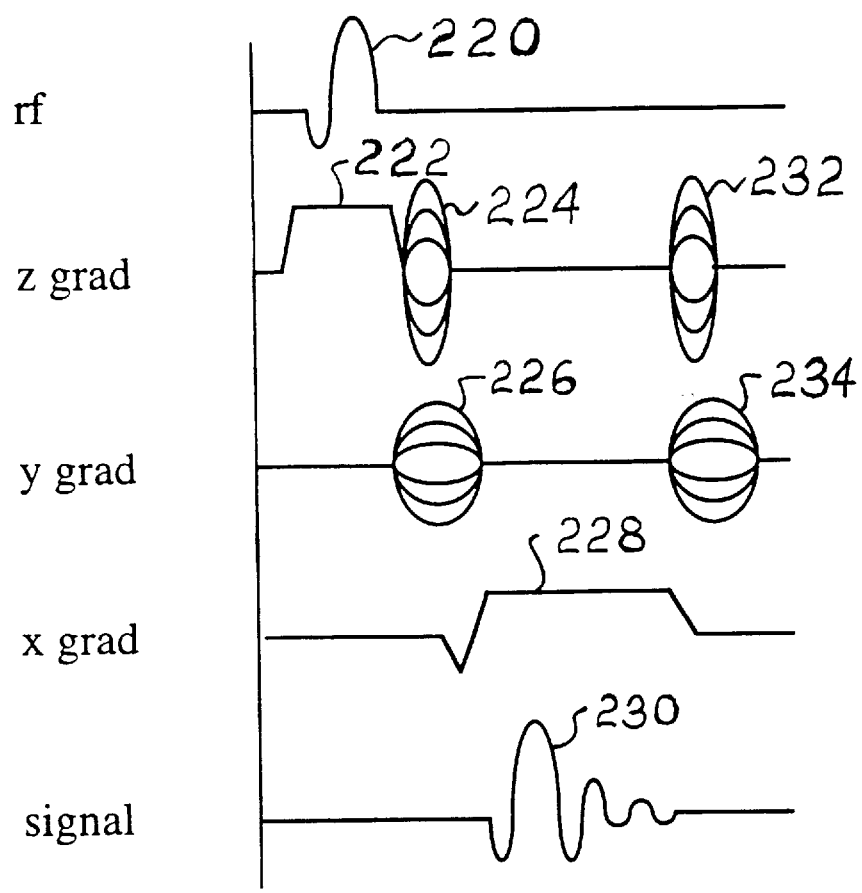
FIG. 3 is a graphic representation of the pulse sequence employed in the preferred embodiment of the invention.

Although the present invention can be used with a number of different pulse sequences, the preferred embodiment of the invention employs a 3D gradient recalled echo pulse sequence depicted in FIG. 3. The pulse sequence "3dfgre" available on the General Electric 1.5 Tesla MR scanner sold under the trademark "SIGNA" with revision level 5.5 system software was used. It was modified to collect data from multiple volumes so that the k-space sampling patterns taught by the present invention can be practiced.

Referring particularly to FIG. 3, an RF excitation pulse 220 having a flip angle of 60° is produced in the presence of a slab select gradient pulse 222 to produce transverse magnetization in the 3D volume of interest as taught in U.S. Pat. No. 4,431,968. This is followed by a phase encoding gradient pulse 224 directed along the z axis and a phase encoding gradient pulse 226 directed along the y axis. A readout gradient pulse 228 directed along the x axis follows and a partial echo (60%) NMR signal 230 is acquired and digitized as described above. After the acquisition, rewinder gradient pulses 232 and 234 rephase the magnetization before the pulse sequence is repeated as taught in U.S. Pat. No. 4,665,365.

Figure 4:
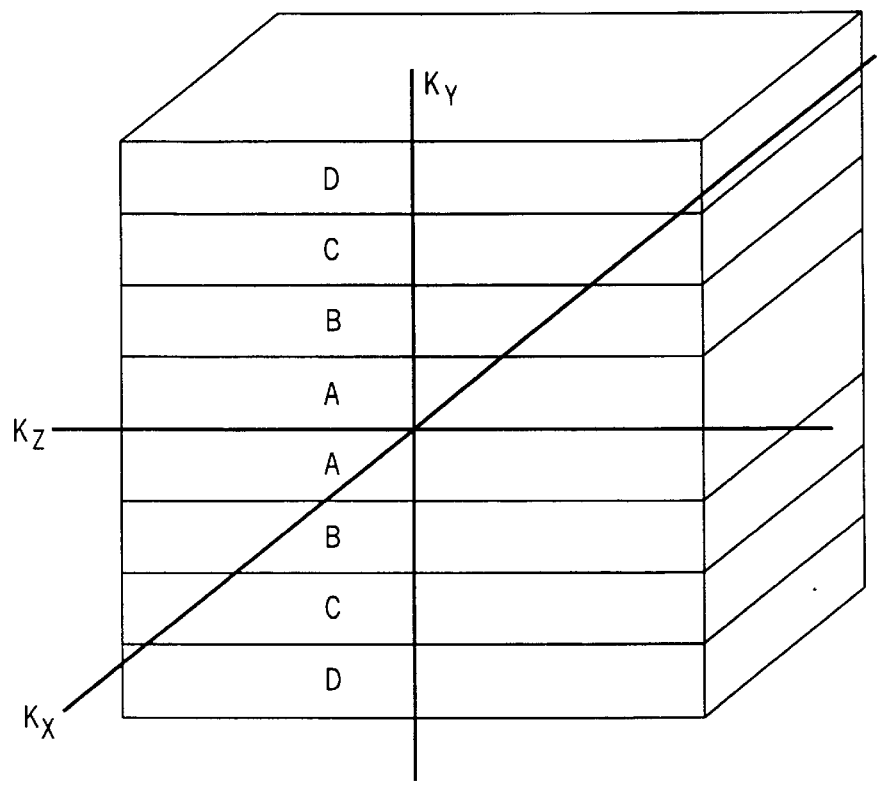
FIG. 4 is a graphic representation of three-dimensional k-space from which data is sampled when practicing the preferred embodiment of the invention.

As is well known in the art, the pulse sequence is repeated and the phase encoding pulses 224 and 226 are stepped through a series of values to sample the 3D k-space depicted in FIG. 4. In the preferred embodiment sixteen phase encodings are employed along the z axis and 128 phase encodings are employed along the y axis. For each particular y phase encoding, therefore, sixteen acquisitions with twelve different z phase encodings are performed to sample completely along the $k_z$ axis. This is repeated 128 times with 128 different y phase encodings to sample completely along the $k_y$ axis. As will become apparent from the discussion below, the order in which this sampling is performed is an important aspect of the present invention.

Sampling along the $k_x$ axis is performed by sampling the echo signal 230 in the presence of the readout gradient pulse 228 during each pulse sequence. It will be understood by those skilled in the art that only a partial sampling along the $k_x$ axis is performed and the missing data is computed using a homodyne reconstruction or by zero filling. This enables the echo time (TE) of the pulse sequence to be shortened to less than 1.8 to 2.0 ms. and the pulse repetition rate (TR) to be shortened to less than 10.0 msecs.

Referring particularly to FIG. 4, to perform a dynamic study according to the present invention the k-space to be sampled is divided into regions. In the preferred embodiment the 3D k-space is divided into four regions designated "A–D". The boundaries of these regions A–D are disposed along the $k_y$ axis and are symmetrical about $k_y=0$. A central region "A" occupies the central k-space region ranging from $k_y=-16$ to +15, and as is well known in the art, these "central" samples contain most of the information which determines the overall contrast in the reconstructed image. As will now be described, it is this central k-space region A which forms the basis for each frame image in the dynamic study and which determine the eventual temporal frame rate.

The remaining three "peripheral" k-space regions B–D are divided and disposed on opposite sides of the central region A. They occupy k-space over the following ranges:

Region B–$k_y=-17$ to −32 and +16 to +31
Region C–$k_y=-33$ to −48 and +32 to +47
Region D–$k_y=-49$ to −64 and +48 to +63.

The central region of k-space be sampled at a higher rate than the peripheral regions during the dynamic study. In the preferred embodiment this is achieved by alternately sampling the central region A and sequential ones of the peripheral regions B–D. Either of the following sampling sequences are thus performed during the dynamic study:

AB AC AD AB AC AD AB AC AD . . .
AD AC AB AD AC AB AD AC AB . . .

Figure 5:
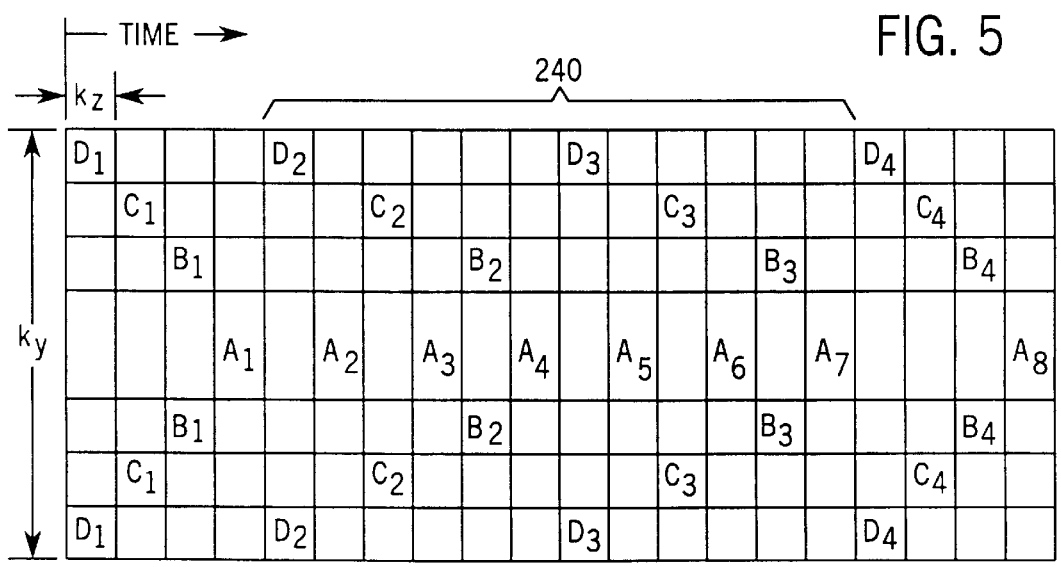
FIG. 5 is a graphic representation of the order in which the three-dimensional k-space of FIG. 4 is sampled.

This latter sampling sequence is shown graphically in FIG. 5, where the horizontal axis indicates real time during the dynamic study and the vertical axis is the region in k-space along the ky axis that is being sampled. The time periods during which each k-space region A–D is sampled are labeled, and the subscripts indicate the number of times the region has been sampled during the dynamic study. It is readily apparent that the central k-space region A is sampled at a higher temporal rate than the peripheral k-space regions B–D.

In this embodiment all of the regions A–D are scanned at the beginning and again at the end of the dynamic study in order to implement other reconstruction strategies to be discussed below. It can be appreciated that the alternating sequence described above is then performed during the critical time period of the dynamic study indicated at 240. This alternating sequence can be extended as long as necessary to encompass the contrast changes of interest that occur during the particular study.

It can be appreciated by those skilled in the art that k-space can be carved up in other ways to practice the present invention. For example, the number of regions can be changed and they can be oriented such that their boundaries are disposed along the slice-select $k_z$ axis. Also, k-space can be divided into a circular central region and a plurality of surrounding, annular-shaped peripheral regions.

Figure 6:
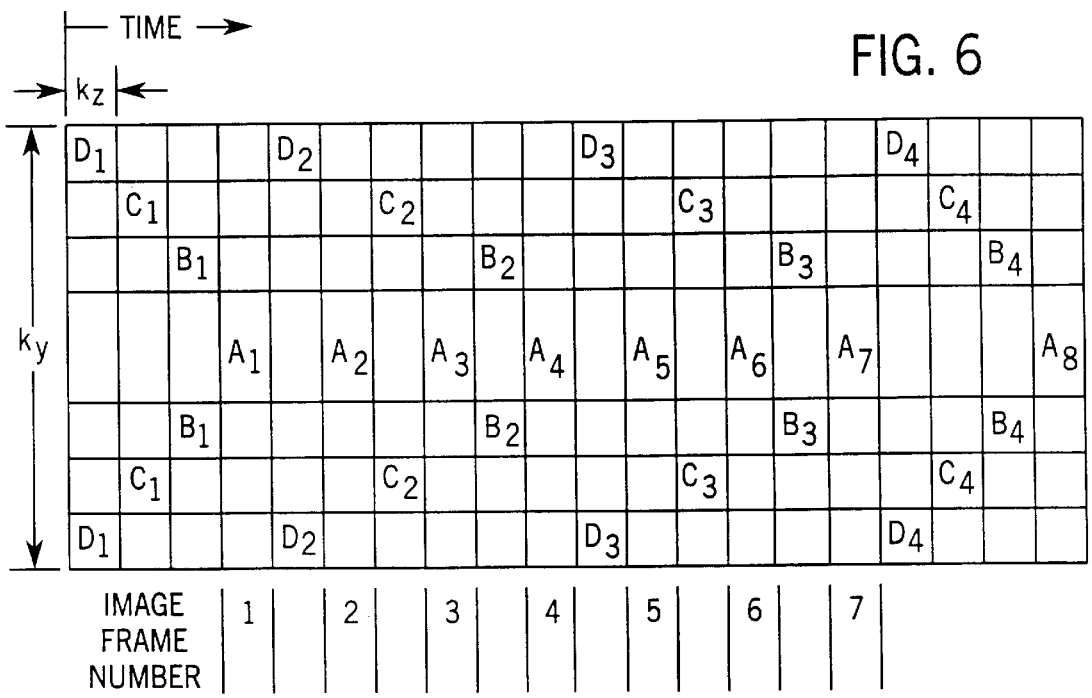
FIG. 6 is a graphic representation of the sampling of the three-dimensional k-space of FIG. 4 showing the times at which each image frame in the dynamic study is reconstructed according to one embodiment of the invention.

The data acquired during the dynamic study can be used in a number of ways to reconstruct a series of frame images $F_1$–$F_n$ that depict contrast changes occurring during the dynamic study. In one embodiment illustrated in FIG. 6, image frames designated $F_1$ through $F_7$ are reconstructed using data from each central k-space region acquisition ($A_1$–$A_7$). This is accomplished by forming a data set sufficient to reconstruct a frame image using the particular central k-space region data combined with temporally adjacent data from the surrounding, peripheral k-space regions B–D. Each image frame data set depicts the subject at a particular time during the dynamic study.

One method for forming each such image frame data set is to use the data acquired from peripheral regions closest in time to the acquisition of the central k-space region A. For frame images $F_2$ through $F_6$ the data acquired and depicted in FIG. 6 may thus be formed into data sets as follows:

$F_2 \rightarrow A_2+B_2+C_2+D_2$
$F_3 \rightarrow A_3+B_2+C_2+(D_2 \text{ or } D_3)$
$F_4 \rightarrow A_4+B_2+(C_2 \text{ or } C_3)+D_3$
$F_5 \rightarrow A_5+(B_2 \text{ or } B_3)+C_3+D_3$
$F_6 \rightarrow A_6+B_3+C_3+(D_3 \text{ or } D_4)$ This method of selecting the data closest in time to that of the image frame is referred to herein as the "nearest neighbor" method. It can be appreciated that sometimes the nearest data for a peripheral region of k-space is close to the frame time, and in other cases the frame time is midway between two sample periods.

Another method for forming a data set at each frame $F_2$ through $F_6$ is to interpolate between the two adjacent sets of data acquired for each peripheral region. A linear interpolation method for forming frame images $F_2$ through $F_6$ from the data acquired and depicted in FIG. 6, for example is as follows:

$F_2 \rightarrow A_2+(B_1+B_2)/2+(4C_2+C_1)/5+(5D_2+D_3)/6$
$F_3 \rightarrow A_3+(5B_2+B_1)/6+(5C_2+C_3)/6+(D_2+D_3)/2$
$F_4 \rightarrow A_4+(5B_2+B_3)/6+(C_2+C_3)/2+(5D_3+D_2)/6$
$F_5 \rightarrow A_5+(B_2+B_3)/2+(5C_3+C_2)/6+(5D_3+D_4)/6$
$F_6 \rightarrow A_6+(5B_3+B_2)/6+(4C_3+C_4)/5+(D_3+D_4)/2$ non-liner interpolation can also be used. For example, if a function indicative of the flow of contrast agent into the region of interest during the dynamic study is determined, this function can be used to weight the sampling done at different times during the study.

In the above-described method for forming data sets from which image frames can be reconstructed, one data set is formed for each sampling of the central region of k-space. Additional image frames can be reconstructed, however, to further increase the temporal resolution of the dynamic study by further interpolation of the acquired data. One method is to simply interpolate between the complete data sets $F_2$–$F_6$ formed as described above. This produces the following additional data sets from which further image frames can be reconstructed:

$F_{2.5}=(F_2+F_3)/2$
$F_{3.5}=(F_3+F_4)/2$
$F_{4.5}=(F_4+F_5)/2$
$F_{5.5}=(F_5+F_6)/2$

Figure 7:
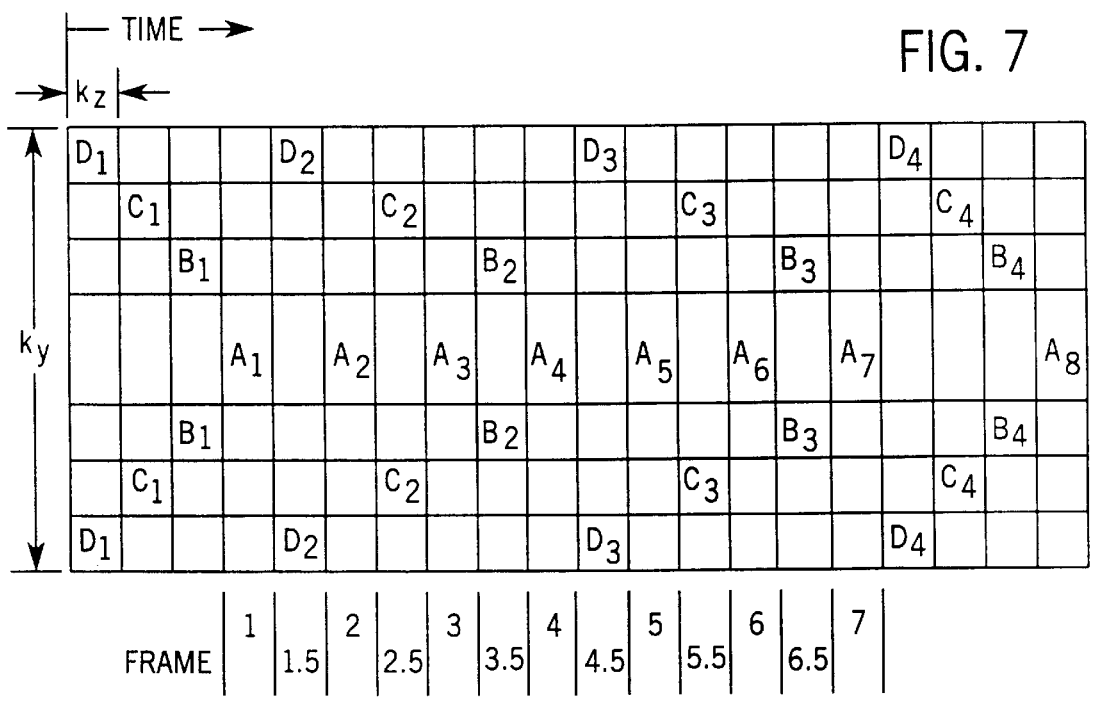
FIG. 7 is a graphic representation of the sampling of the three-dimensional k-space of FIG. 4 showing the times at which each image frame in the dynamic study is reconstructed according to a second embodiment of the invention.

However, the preferred method is to completely form the additional, intermediate image frame data sets directly from the acquired sample data. Referring particularly to FIG. 7, this is achieved by interpolating between successive sample data for the central k-space region and interpolating between the successive the peripheral k-space region samples. These intermediate data sets may thus be formed as follows:

$F_{1.5} \rightarrow I_{1.5}(A_1, A_2) + I_{1.5}(B_1, B_2) + I_{1.5}(C_1, C_2) + D_2$ $F_{2.5} \rightarrow I_{2.5}(A_2, A_3) + I_{2.5}(B_1, B_2) + C_2 + I_{2.5}(D_2, D_3)$ $F_{3.5} \rightarrow I_{3.5}(A_3, A_3) + B_2 + I_{3.5}(C_2, C_3) + I_{3.5}(D_2, D_3)$ $F_{4.5} \rightarrow I_{4.5}(A_4, A_5) + I_{4.5}(B_2 + B_3) + I_{4.5}(C_2, C_3) + D_3$ $F_{5.5} \rightarrow I_{5.5}(A_5, A_6) + I_{5.5}(B_2, B_3) + C_3 + I_{5.5}(D_3, D_4)$ $F_{6.5} \rightarrow I_{6.5}(A_6, A_7) + B_3 + I_{6.5}(C_3, C_4) + I_{6.5}(D_3, D_4)$ where "I" is the interpolation method used to calculate the k-space sample data at the desired frame time from the corresponding temporally adjacent k-space samples.

Regardless of how they are formed, the image frame data sets are employed to reconstruct a corresponding set of 3D frame images. In the preferred embodiment a three-dimensional Fourier transformation method is used to reconstruct each 3D frame image. Six such 3D frame images are shown in FIG. 8 as frame image data sets 250–255. A number of different procedures can be used to produce useful diagnostic images from these frame image data sets 250–255.

While images may be produced simply by selecting a set of data points located in a cross section through one of the 3D data arrays 250–255, such images have limited diagnostic value. This is because blood vessels usually do not lie in a single plane and such cross sectional images show only short pieces or cross sections of many vessels that happen to pass through the selected plane. Such images are useful when a specific location in a specific vessel is to be examined, but they are less useful as a means for examining the health of the vascular system and identifying regions that may be diseased.

For assessing overall blood vessel structure and health it is more useful to project the 3D array of NMR data into a single 2D projection image to produce an angiogram-like picture of the vascular system. The most commonly used technique for doing this is to project a ray from each pixel in the projection image through the array of data points and select the data point which has the maximum value. The value selected for each ray is used to control the brightness of its corresponding pixel in the projection image. This method, referred to hereinafter as the "maximum pixel technique," is very easy to implement and it gives aesthetically pleasing images. It is presently the preferred method.

The 2D projection images from each 3D image frame data set 250–255 is shown in FIG. 8 at 260–265. These may be viewed directly and used to observe the flow of contrast agent into the subject vasculature over the time course of the dynamic study. These images enable the radiologist to select the 3D image frame data set from which a difference image according to the present invention is reconstructed. A difference projection image is produced by selecting two of the 3D image frame data sets 250–255 and calculating the difference between their corresponding pixel values. It is a teaching of the present invention that one of the chosen 3D image frame data sets that is to be subtracted from another data set is a mask data set formed from samples of the central k-space region only. It has been discovered that if one of the early image frames is used as a subtraction mask, it may contain common samples from the peripheral regions (B, C or D) used to form the desired image frame. When subtracted, therefore, the high spatial frequency content of the resulting difference image may be reduced.

Accordingly, the subtraction mask selected from one of the 3D image frame data sets 250–255 is formed by using only NMR data sampled from the central k-space region A. This low spatial frequency mask is sufficient to subtract out the large area tissue signals which, especially when enhanced by previous injections of contrast agent, can cause serious image artifacts in the difference image. This can occur, for example, when the projection method used to produce a 2D image chooses a bright pixel in the enhanced stationary tissue rather than an artery of interest.

A 3D difference image is produced as indicated by data set 270 and this is then used to produce a 2D difference projection image 272 using the same projection method described above. The selection of two 3D image frame data sets 250–255 is made by the diagnostician to enhance the image contrast in the particular vasculature of interest. Since it is difficult to predict exactly when the peak contrast agent flow will occur through the subject vasculature, the series of 3D image frames provides a time range during which this event should occur.

There are several reasons why image subtraction and other temporal processing techniques are useful. When multiple injections are done, the non-vascular background becomes very bright, lowering vessel to background contrast. Subtraction of an early frame prior to vascular opacification will remove the background. Subtraction is also useful for creating additional opportunities to obtain images where veins and arteries display separately. Often a late image, containing only veins, can be subtracted from an earlier image in which the arterial signal is superimposed on the venous signal, creating an arterial image. Regardless of the selection, the subtraction mask should be formed only from samples from the central region A of k-space to avoid reduction of high spatial frequency information.

We claim:

1. A method for producing a contrast enhanced NMR image with an MRI system that performs a pulse sequence which samples a region of k-space, the steps comprising:

a) acquiring a mask NMR data set by performing the pulse sequence to sample only a central portion of said k-space;

b) acquiring an NMR image data set by performing the pulse sequence to sample said central portion of said k-space and a peripheral portion of said k-space;

c) producing a difference data set by subtracting the mask NMR data set from the image NMR data set; and d) reconstructing the NMR image from the difference data set.

2. The method as recited in claim 1 in which the mask NMR data set and the NMR image data set are acquired during a dynamic study of a subject after injection of a contrast agent.

3. The method as recited in claim 2 in which the pulse sequence is repeatedly performed during the dynamic study to form a plurality of acquired NMR data sets, the mask NMR data set is selected from one of the acquired NMR data sets, and the NMR image data set is selected from another one of the acquired NMR data sets.

4. The method as recited in claim 1 in which the pulse sequence is performed a plurality of times to acquire the mask NMR data set, and the pulse sequence is performed a plurality of times to acquire the NMR image data set.

* * * * *